US011380433B2

(12) United States Patent
Palma et al.

(10) Patent No.: US 11,380,433 B2
(45) Date of Patent: Jul. 5, 2022

(54) OPTIMIZED DATA COLLECTION OF RELEVANT MEDICAL IMAGES

(71) Applicant: International Business Machines Corporation, Armonk, NY (US)

(72) Inventors: Giovanni John Jacques Palma, Chaville (FR); Thomas Binder, Paris (FR); Frederic Commandeur, Paris (FR)

(73) Assignee: International Business Machines Corporation, Armonk, NY (US)

( * ) Notice: Subject to any disclaimer, the term of this patent is extended or adjusted under 35 U.S.C. 154(b) by 61 days.

(21) Appl. No.: 17/034,946

(22) Filed: Sep. 28, 2020

(65) Prior Publication Data

US 2022/0101982 A1 Mar. 31, 2022

(51) Int. Cl.
*G06K 9/00* (2022.01)
*G16H 30/40* (2018.01)
(Continued)

(52) U.S. Cl.
CPC ............. *G16H 30/40* (2018.01); *G06N 20/00* (2019.01); *G06T 3/4046* (2013.01);
(Continued)

(58) Field of Classification Search
CPC ........ G16H 30/40; G16H 50/20; G06N 20/00; G06T 3/4046; G06T 7/0014;
(Continued)

(56) References Cited

U.S. PATENT DOCUMENTS 10,360,675 B2 7/2019 Reicher et al.
2013/0216094 A1 8/2013 Delean
(Continued)

FOREIGN PATENT DOCUMENTS

| CN | 107346336 A | 11/2017 |
|----|-------------|---------|
| EP | 3641635 A1 | 4/2020 |
| WO | 2019119030 A1 | 6/2019 |

OTHER PUBLICATIONS

Stember et al., "Eye Tracking for Deep Learning Segmentation Using Convolutional Neural Networks", Journal of Digital Imaging, vol. 32, 2019, pp. 597-604, <https://link.springer.com/article/10.1007/s10278-019-00220-4>.
(Continued)

*Primary Examiner* — Xin Jia
(74) *Attorney, Agent, or Firm* — Stephanie L. Carusillo

(57) ABSTRACT

Some embodiments of the present invention select image data that are valuable for developing and/or training a deep learning based algorithm. A semi-automated system identifies cases that are the most valuable (most impactful, useful, and/or most effective) for developing and/or training the deep learning algorithm. The semi-automated system monitors a degree of uncertainty in the results produced by an
(Continued)

image processing algorithm. Cases where the degree of uncertainty is high, and consequently a confidence score is low, are made ready for analysis, classification, and/or annotation by human review. Once analyzed, classified and/or annotated by human review, the data is made available for use in developing and/or training the deep learning algorithm.

20 Claims, 3 Drawing Sheets

(51) Int. Cl.
 *G16H 50/20* (2018.01)
 *G06T 7/00* (2017.01)
 *G06T 3/40* (2006.01)
 *G06N 20/00* (2019.01)

(52) U.S. Cl.
 CPC .......... *G06T 7/0014* (2013.01); *G16H 50/20* (2018.01); *G06T 2200/24* (2013.01); *G06T 2207/20081* (2013.01); *G06T 2207/20084* (2013.01); *G06T 2207/30004* (2013.01)

(58) Field of Classification Search
 CPC ....... G06T 2200/24; G06T 2207/20081; G06T 2207/20084; G06T 2207/30004
 See application file for complete search history.

(56) References Cited

U.S. PATENT DOCUMENTS

| | | |
|---|---|---|
| 2017/0039452 A1 | 2/2017 | Osindero |
| 2018/0144244 A1 | 5/2018 | Masoud et al. |
| 2019/0065848 A1 | 2/2019 | Borrel |
| 2019/0130074 A1* | 5/2019 | Itu .............................. G06T 7/60 |
| 2019/0139642 A1 | 5/2019 | Roberge et al. |
| 2019/0156526 A1* | 5/2019 | Liu ........................... G06T 7/90 |
| 2020/0069973 A1* | 3/2020 | Lou ...................... A61B 6/5211 |
| 2020/0161005 A1* | 5/2020 | Lyman ................. G06K 9/6274 |

OTHER PUBLICATIONS

"Patent Cooperation Treaty PCT International Search Report", Applicant's File Reference: P202001963PCT01, International Application No. PCT /IB2021/058675, International Filing Date: Sep. 23, 2021, dated Jan. 13, 2022, 8 pages.

* cited by examiner

OPTIMIZED DATA COLLECTION OF RELEVANT MEDICAL IMAGES

BACKGROUND

The present invention relates generally to the field of automated image processing, and more particularly to providing effective example data used for development and training of automated image processing algorithms.

Machine learning/deep learning based algorithms are becoming popular in many fields including in medical image analysis. Machine learning/deep learning based algorithms rely on availability of qualitative, annotated data for training the learning algorithms.

SUMMARY

According to an aspect of the present invention, there is a method, computer program product and/or system that performs the following operations (not necessarily in the following order): (i) analyzing a first set of images, including a first image, at an image manipulation stage, wherein the image manipulation stage comprises an image processing algorithmic chain; (ii) extracting a plurality of relevant features derived from the analysis at the image manipulation stage, including a first extracted relevant feature with respect to the first image; (iii) computing a plurality of degrees of interest, including a first degree of interest, with respect to the plurality of extracted relevant features; (iv) determining a subset of the first set of images wherein a respectively corresponding plurality of degrees of interest exceed a threshold; and (v) in response to determining the subset of the first set of images, sending the subset of the first set of images to a receiving system.

DETAILED DESCRIPTION

Figure 1:
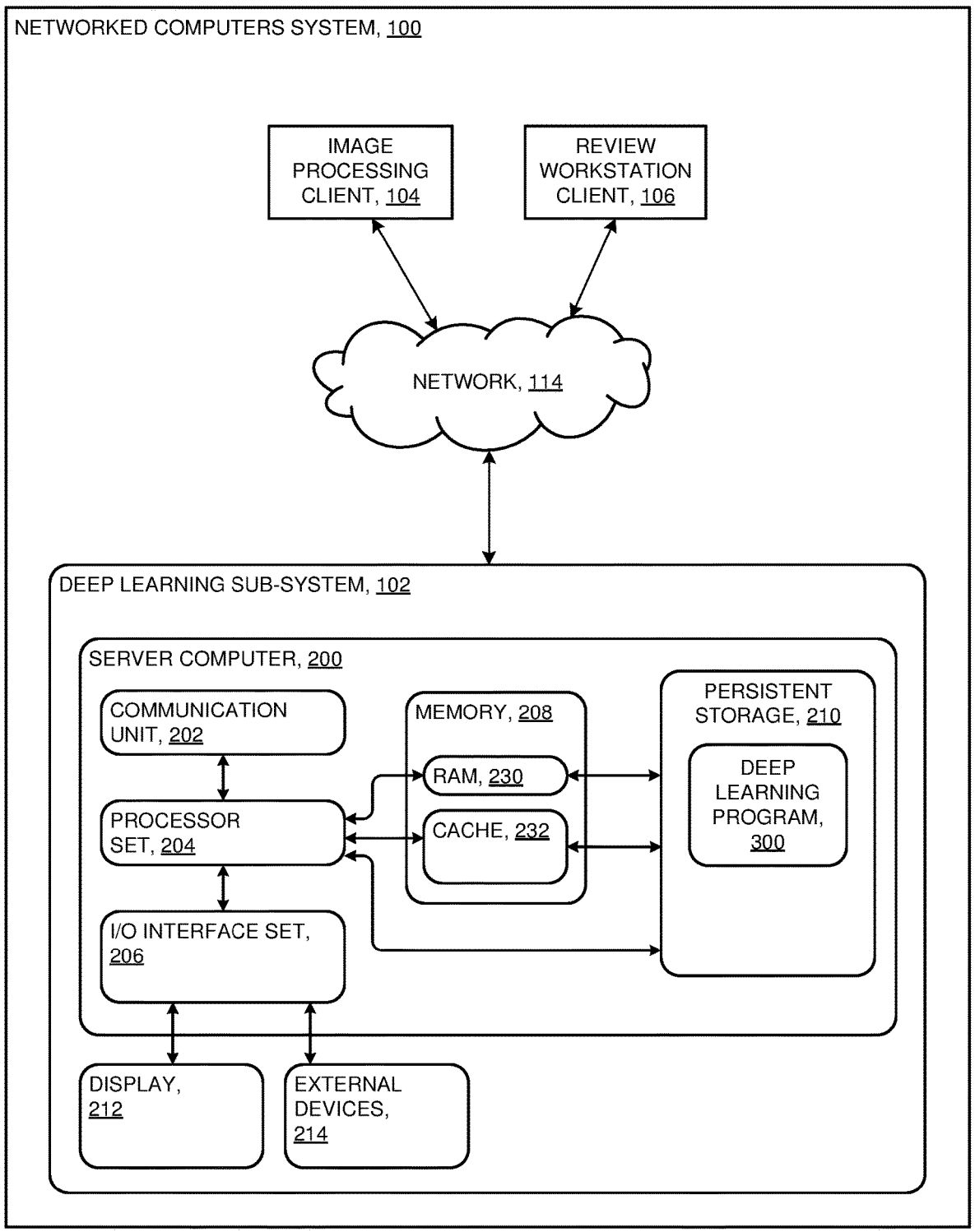
FIG. 1 is a block diagram of a embodiment of a system in accordance with at least one embodiment of the present invention.

Development and performance of a deep learning algorithm depends in part on the quality of data used for the learning. Some data are more beneficial to the learning process than other data. Over-represented and obvious cases may have little impact on learning performance. Focusing on difficult cases where the algorithm struggles to make decisions may be more impactful and beneficial to learning performance.

Some embodiments of the present invention provide a means to collect data that are the most valuable for developing and/or training a (machine learning) deep learning based algorithm. A semi-automated system identifies cases that are the most valuable (most impactful, useful, and/or most effective) for training the deep learning algorithm. The system monitors a degree of uncertainty in results produced by an image processing algorithm, for cases that are processed routinely. Cases where the degree of uncertainty is high (and consequently a confidence score is low, sometimes called "difficult" cases), are made ready for analysis, classification, and/or annotation by human reviewers. Once analyzed, classified and/or annotated, the data is made available for use in developing and/or training the deep learning based algorithm.

Moreover, some embodiments facilitate a review and annotation workflow by analyzing certain aspects of the review process used by a human expert (in a medial field for example, a radiologist, oncologist or other specialist), for cases of interest, to pre-determine outcomes of respective cases (for example to determine certain clinical information such as presence of lesion, area of focus, etc.).

Some embodiments of the present invention comprise a process for training a deep learning algorithm to perform certain automated image analysis tasks. One example of such a task is classifying a lesion in a medical image as to whether the lesion is malignant or benign. In some images, the classification is difficult to perform. The deep learning algorithm may produce conflicting results, and/or compute a relatively low confidence level associated with a result. Embodiments of the present invention analyze large volumes of images to identify images for which the image analysis task is difficult. The images so identified are presented for human expert review and classification, the results of which are made available for use in developing and/or training the deep learning algorithm.

This Detailed Description section is divided into the following sub-sections: (i) The Hardware and Software Environment; (ii) Example Embodiment; (iii) Further Comments and/or Embodiments; and (iv) Definitions.

I. THE HARDWARE AND SOFTWARE ENVIRONMENT

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

An embodiment of a possible hardware and software environment for software and/or methods according to the present invention will now be described in detail with reference to the Figures. FIG. 1 is a functional block diagram illustrating various portions of networked computers system 100, including: deep learning sub-system 102; image processing client 104; review workstation 106; communication network 114; server computer 200; communication unit 202; processor set 204; input/output (I/O) interface set 206; memory 208; persistent storage 210; display 212; external devices 214; random access memory (RAM 230); cache 232; and program 300.

Deep learning sub-system 102 is, in many respects, representative of the various computer sub-system(s) in the present invention. Accordingly, several portions of deep learning sub-system 102 will now be discussed in the following paragraphs.

Deep learning sub-system 102 may be a laptop computer, tablet computer, netbook computer, personal computer (PC), a desktop computer, a personal digital assistant (PDA), a smart phone, or any programmable electronic device capable of communicating with the client sub-systems via communication network 114. Program 300 is a collection of machine readable instructions and/or data that is used to create, manage, and control certain software functions that will be discussed in detail, below, in the Example Embodiment sub-section of this Detailed Description section.

Deep learning sub-system 102 is capable of communicating with other computer sub-systems via communication network 114. Communication network 114 can be, for example, a local area network (LAN), a wide area network (WAN) such as the Internet, or a combination of the two, and can include wired, wireless, or fiber optic connections. In general, communication network 114 can be any combination of connections and protocols that will support communications between server and client sub-systems.

Deep learning sub-system 102 is shown as a block diagram with many double arrows. These double arrows (no separate reference numerals) represent a communications fabric, which provides communications between various components of deep learning sub-system 102. This communications fabric can be implemented with any architecture designed for passing data and/or control information between processors (such as microprocessors, communications and network processors, etc.), system memory, peripheral devices, and any other hardware components within a system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external devices 214 may be able to supply, some or all, memory for deep learning sub-system 102; and/or (ii) devices external to deep learning sub-system 102 may be able to provide memory for deep learning sub-system 102.

Program 300 is stored in persistent storage 210 for access and/or execution by one or more of the respective computer processor set 204, usually through one or more memories of memory 208. Persistent storage 210: (i) is at least more persistent than a signal in transit; (ii) stores the program (including its soft logic and/or data), on a tangible medium (such as magnetic or optical domains); and (iii) is substantially less persistent than permanent storage. Alternatively, data storage may be more persistent and/or permanent than the type of storage provided by persistent storage 210.

Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communication unit 202, in these examples, provides for communications with other data processing systems or devices external to deep learning sub-system 102. In these examples, communication unit 202 includes one or more network interface cards. Communication unit 202 may provide communications through the use of either or both physical and wireless communications links. Any software modules discussed herein may be downloaded to a persistent storage device (such as persistent storage 210) through a communications unit (such as communication unit 202).

I/O interface set 206 allows for input and output of data with other devices that may be connected locally in data communication with server computer 200. For example, I/O interface set 206 provides a connection to external devices 214. External devices 214 will may include devices such as a keyboard, keypad, a touch screen, and/or some other suitable input device. External devices 214 can also include portable computer-readable storage media such as, for example, thumb drives, portable optical or magnetic disks, and memory cards. Software and data used to practice embodiments of the present invention, for example, program 300, can be stored on such portable computer-readable storage media. In these embodiments, the relevant software may (or may not) be loaded, in whole or in part, onto persistent storage 210 via I/O interface set 206. I/O interface set 206 also connects in data communication with display 212.

Display 212 provides a mechanism to display data to a user and may be, for example, a computer monitor or a smart phone display screen.

The programs described herein are identified based upon the application for which they are implemented in a specific embodiment of the invention. However, it should be appreciated that any particular program nomenclature, herein, is used merely for convenience, and, thus, the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. EXAMPLE EMBODIMENT

Figure 2:
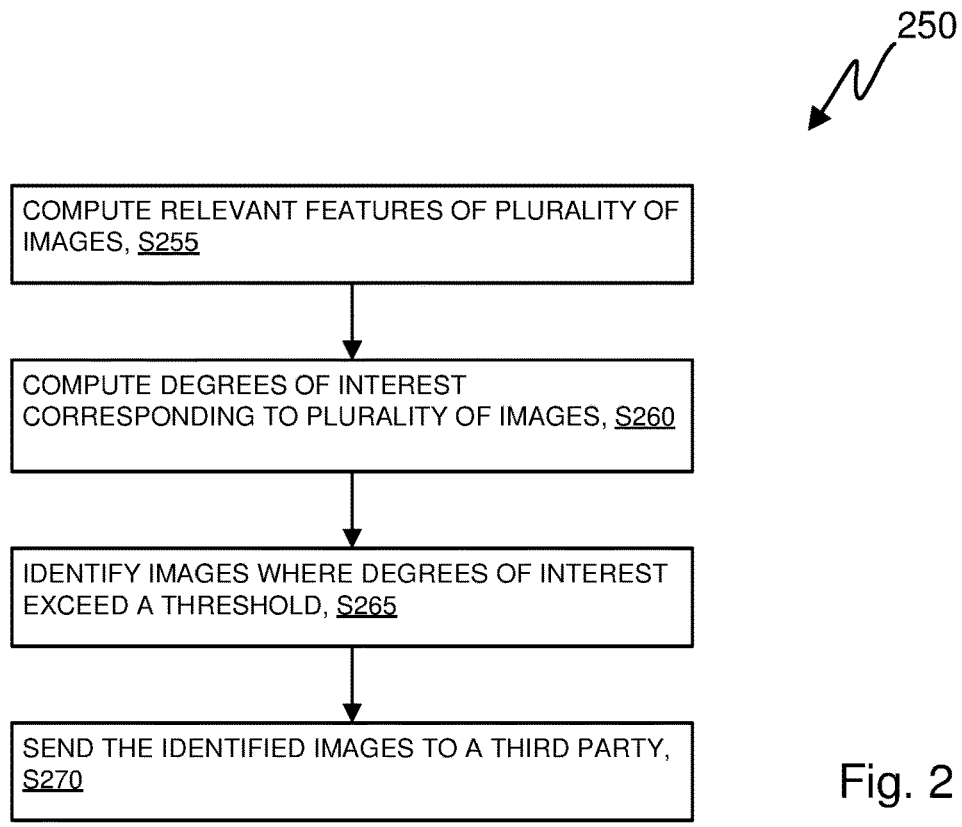
FIG. 2 is a flowchart showing a method performed, at least in part, in accordance with at least one embodiment of the present invention.
Figure 3:
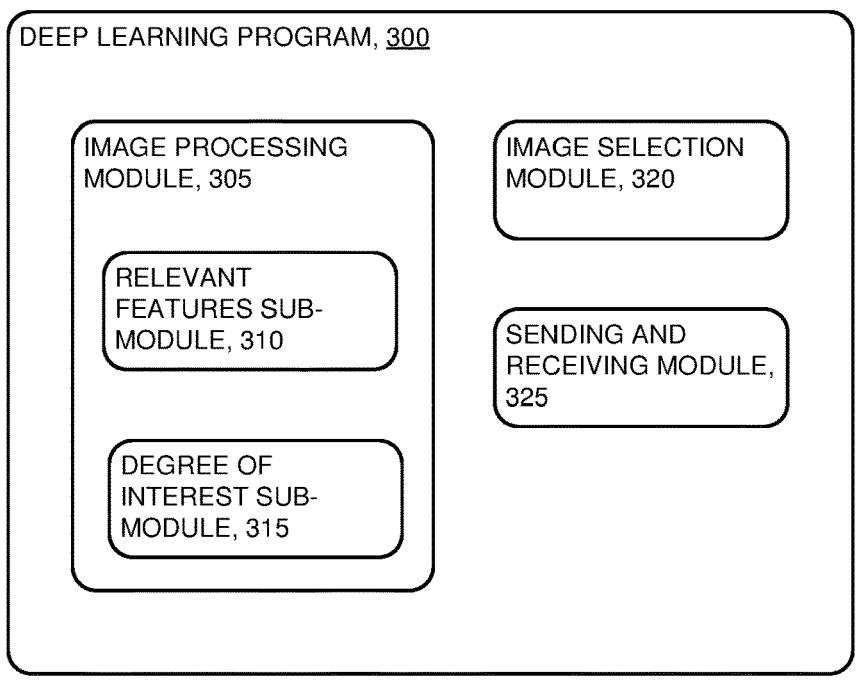
FIG. 3 is a block diagram showing a machine logic (for example, software) portion of a system in accordance with at least one embodiment of the present invention.

FIG. 2 shows flowchart 250 depicting a method according to the present invention. FIG. 3 shows program 300 for performing at least some of the method operations of flowchart 250. This method and associated software will now be discussed, over the course of the following paragraphs, with extensive reference to FIG. 2 (for the method operation blocks) and FIG. 3 (for the software blocks).

Processing begins at operation S255, where relevant features sub-module 310, of image processing module 305, of deep learning program 300, determines one or more relevant features in each of a plurality of images. For example, in a medical context, a relevant feature may be a lesion shown in a computed tomography (CT) scan image. In a failure analysis context, a relevant feature may be an unusual grain structure shown in a metallograph of a failed aircraft component. In some embodiments, relevant features sub-module 310 correlates other information (for example, other diagnostic information associated with the patient from whom the image was obtained) associated with each image to help determine the one or more relevant features in each image.

Processing proceeds at operation S260, where degree of interest sub-module 315, of image processing module 305, of deep learning program 300, determines a degree of interest corresponding to each image of the plurality of images. A degree of interest is related to the uncertainty associated with a given analysis. For example, in a medical context, if relevant features sub-module 310 identifies an area in an image as representing a lesion, but determines that there is a low degree of confidence that it is in fact a lesion, the corresponding degree of interest is high. In other words, it is "difficult" for relevant features sub-module 310 to determine if the artifact is a lesion or not. Thus, "difficult" cases are useful for efficiently teaching deep learning program 300 to distinguish a lesion (or any other "difficult to identify" characteristic in any context) from a non-lesion artifact with a high degree of confidence.

Processing proceeds at operation S265, where image selection module 320 of deep learning program 300, selects images having a high degree (above a predetermined threshold) of interest as determined in operation S260 above. These are termed "interesting" images.

Processing proceeds at operation S270, where sending and receiving module 325 of deep learning program 300 sends the interesting images determined in operation S265 to a designated repository.

A human expert, for example a radiologist (or a team of experts), evaluates some or all of the "interesting" images to assign corresponding diagnoses and/or annotate the images as appropriate. In some embodiments, the annotated images and/or diagnoses are returned, via sending and receiving module 325, to deep learning program 300, whereupon deep learning program 300 teaches relevant features sub-module 310 to better classify "difficult" images.

III. FURTHER COMMENTS AND/OR EMBODIMENTS

Some embodiments of the present invention comprise new software process to select certain images to feed into a deep learning algorithm, for training an image processing algorithm in a quick and efficient manner. The images selected to have the greatest impact on the training as opposed to routine images that have only marginal, or no, impact on the training. In other words, initial training using routine images contributes to the training but eventually run up against diminishing returns for continued training. In contrast, images selected in accordance with some embodiments of the present invention overcome the otherwise diminishing returns issue.

Some embodiments input random images into an image manipulation software tool (sometimes herein referred to as an image manipulation stage), which analyzes each of the images. In some embodiments, the software tool comprises a viewer which shows the images to a human user. In some embodiments, the software tool comprises a CAD system which processes the images. The human user and/or CAD system interact with each image, and the software tool analyzes aspects of the interactions.

In some embodiments, the software tool makes use of an image processing algorithmic chain. The image processing algorithmic chain comprises one or more internal operations such as (without limitation): (i) detecting a finding in an image; (ii) classifying the finding the image; and/or (iii) classifying the image.

In a case where a human user views the images, a system in accordance with some embodiments, analyzes the interactions that the human user makes with each image (note: the interactions of the user are with a user interface of the display device through which the user views the image). Interactions comprise events and actions taken by the user such as magnifying the image, shrinking the image, focusing on a particular area of the image, time spent viewing the image, the nature of any annotations made by the user, measuring some aspect of the image (such as the size of a lesion, an optical density of an area of the image, a spatial density of some artifact of the image, etc.). The system is given a set of predetermined criteria associated with such events and actions, and compares the results of the interaction analysis to the set of criteria. If some or all of the criteria are met (for example, if the human user views an image for more than 30 seconds and/or magnifies the image), then the image is deemed to be "interesting". "Interesting" images are then provided as input into the deep learning algorithm, which may use the images to continue and enhance training of the deep learning algorithm.

Figure 4:
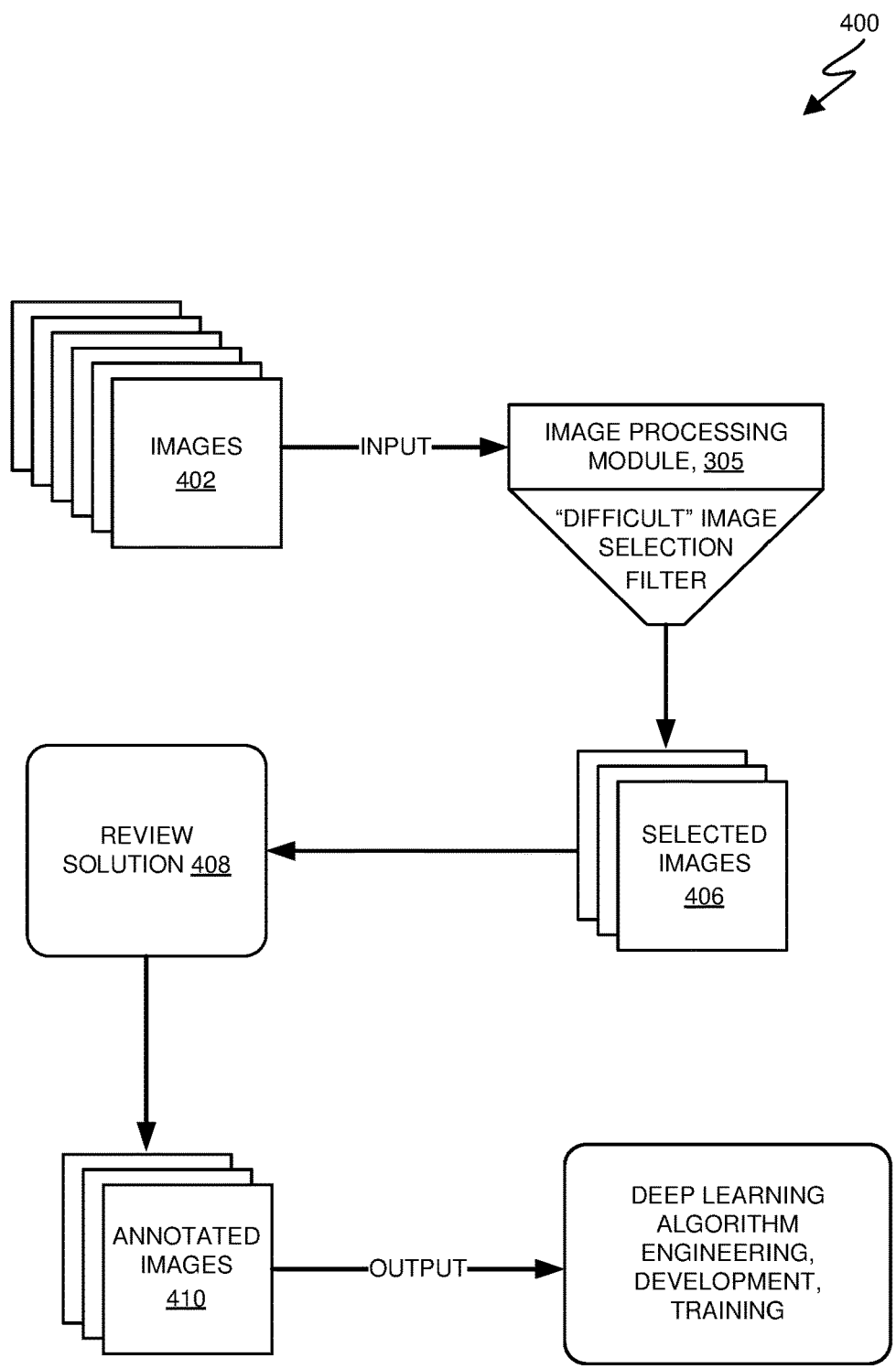
FIG. 4 is a block diagram showing a workflow in accordance with at least one embodiment of the present invention.

Block diagram 400 of FIG. 4, shows a system workflow in accordance with some embodiments of the present invention. Images 402 include a large number of images of a subject matter for which deep learning program 300 (see FIG. 3) is to be trained to analyze and properly classify. Images 402 comprises input into the system workflow. Many individual images of images 402 are easily analyzed and properly classified with a high confidence level, by image processing module 305, of deep learning program 300 (see FIG. 3).

A subset of images 402 (herein referred to as "difficult" images) are not easily classified, by image processing module 305 and a low confidence level attaches to the consequent results. Image processing module 305 acts as a selection filter to identify the "difficult" images. The "difficult" images are selected based, at least in part, on respective confidence levels attached to each result. Images with low confidence levels are selected to proceed along the workflow. Methods for determining confidence levels varies from one embodiment to another, as does confidence threshold levels used for determining whether an image is "difficult" or not (whether an image passes through the selection filter).

In some embodiments of the present invention, a confidence measure is based on values such as (without limitation): (i) a distance between the output of an operation to detect a finding, and a reference or given value; (ii) a distance between the output of an operation to classify a finding, and a reference or given value; (iii) discrepant outputs produced by a plurality of operations that perform the same task; and/or (iv) a probability that input data for an internal operation, is represented in data used for training a deep learning model corresponding to the internal operation.

Images determined to be "difficult", comprising selected images 406, are passed on to review solution 408. Review solution 408 comprises at least: (i) means for displaying each image to a human reviewer; (ii) a user interface such that the human reviewer can interact with review solution 408, apply to an image such things as annotations, measurements, remarks, and/or other indications with respect to proper classification of the image; and/or (iii) means for sending each image to an automated system for analysis by machine. In some embodiments, review solution 408 is any system capable of displaying images for viewing by the user, accepting and responding to user input.

Images processed through review solution 408, now referred to as annotated images 410, comprise the system workflow output, and are made available for use in developing and training deep learning program 300 (see FIG. 3) and image processing algorithms incorporated therein.

Use case example #1. In some embodiments, a radiologist sends a clinical case (diagnostic images such as computed tomography scans (CT scan, or CAT scan), magnetic resonance images (MM), ultrasound images, X-ray images, etc.) to an automated image analysis tool such as a computer aided design (CAD) system. An algorithm of the automated image analysis tool, operating in conjunction with the CAD system, computes clinical information such as lesion detection, organ segmentation, pathology classification, etc. The algorithm further computes internal confidence levels associates with decision(s) it makes. For instance, when classifying a lesion as to whether it is malignant or benign, the algorithm computes two confidence scores respectively corresponding to conclusions of malignancy or benignancy. If the two scores are close to each other (within a predetermined threshold), it means the system is unable to come to a decision with an acceptable level of confidence. The algorithm classifies cases having low confidence levels as potentially "interesting" cases. Subsequently, one or more medical specialists may then review interesting cases, come to appropriate diagnoses (either individually, or by consensus with one another). In some embodiments, the diagnoses are then fed back to the algorithm of the automated image analysis tool, for training (machine learning) to refine and improve the algorithm.

Use case/example #2. A radiologist, or other medical specialist, sends a clinical case (that is, a diagnostic image) to an automated image analysis tool such as a computer aided design (CAD) system. An algorithm of the automated image analysis tool, operating in conjunction with the CAD system computes clinical information such as lesion detection, organ segmentation, pathology classification, etc. The image analysis tool sends back the result to a review solution, such as a workstation. The radiologist interacts with the workstation to analyze the case and determine a diagnosis or make a conclusion of one sort or another. The review solution measures, records, and analyzes certain metrics (termed "user interaction analysis) associated with the interactions of the radiologist with the workstation. If the two sources of clinical information (results determined by the algorithm and the radiologist) disagree (are in conflict with one another), the case is identified as a potentially interesting case. One or more medical specialists may then review interesting cases, come to appropriate conclusions and/or diagnoses (either individually, or by consensus with one another). In some embodiments, The review solution feeds the results back to the algorithm of the automated image analysis tool, to refine and improve the algorithm via machine deep learning. In some embodiments, the user interaction analysis, and consequent mapping to clinical information is performed using machine learning.

Methods for determining a degree of interest associated with an image, in accordance with some embodiments of the present invention, are presented in the following enumerated paragraphs:

(i) Provided: A computer aided design (CAD) algorithm, with a classification stage that gives a probability, ranging from 0 to 1, for each class. Principle: Determines, for each classification output, a confidence level (a level of uncertainty) for the classification. Metric (M): $M=\|p-0.5\|$, where p is the classifier output(s). Note: $\|x\|$ represents the "norm" of x, in the field of mathematics.

(ii) Provided: A CAD algorithm with a detection stage (for example, a voxel-wise map of detection of lesions). Principle: Areas of predicted voxel that are neither 0 nor 1 are ambiguous. Metric: $M=\text{Average}(\|P_x-0.5\|)$, where $P_x$ is the predicted map at voxel x. In some embodiments, P is the predicted map itself, whereas in some embodiments, P is the result of postprocessing (for example, eroded/dilated version to avoid counting imprecision from lesion boundaries). Some embodiments use aggregation methods other than average (such as maximum, minimum, median, mode, etc.). Note: a voxel is a volume element in a three-dimensional volume (or higher-dimensional volume), analogous to a pixel in a two-dimensional image.

(iii) Provided: An algorithm of a CAD system uses an encoder (low dimension feature space). Principle: A distribution of the features of the training data can be computed beforehand. An outlier of that distribution is an unseen case. Metric: $M=p(E(V))$, where V is the case (that is a volume) to process, E is the encoder of the volume to a lower dimension space, and p is the probability density function estimated on the training data.

(iv) Provided: A case is being processed within a user interface (UI). Principle: Complex cases may require unusual lengths of time to be read and processed by a human reviewer, and/or may involve additional review actions (such zooming in to focus on a particular area of interest). Metric: $M=t\Sigma a_i$, where $a_i$ are weights associated with respectively corresponding user actions, t is the elapsed review time taken, and $\Sigma$ is the summation function. In some embodiments, time is not considered a factor, and the metric is thus $M=\Sigma a_i$.

(v) Provided: A CAD algorithm uses an ensemble of several prediction models performing the same task. Principle: If two or more prediction models disagree, the case may be considered a difficult case. Metric: $M=\text{var}(p_i)$ where $p_i$ are the output of all the models doing the same task, and var( ) is a statistical variance function $$\frac{1}{n}\sum_{i=1}^{n}(p_i-\mu)^2,$$

where n is the number of models, and $\mu$ is the mean of the outputs from all the models ($\mu=\Sigma_{i=1}^{n}p_i$). In an embodiment that uses two prediction models only, a difficult case is considered one in which the two prediction models produce results that differ by more than a threshold amount t, where $t<|p_1-p_2|$. Some embodiments replace var( ) with other statistical metrics such as entropy, range, etc.

(vi) Provided: A CAD algorithm. Principle: Each component should be stable given slight variation of the input. Metric: $M=\|P(V)-A^{-1}P(A(V))\|$, where P is a model or a set of models from the CAD chain, A is an augmentation process, $A^{-1}$ the inverse process, and V is the input data (for example, a volume). Note: in classification tasks in some embodiments, $A^{-1}$ is omitted and consequently, $M=\|P(V)-P(A(V))\|$. Augmentation functions include, for example, deformation, rotation, zoom, etc.

(vii) Provided: A CAD tool and a report. Principle: Ideally, the report and the CAD tool algorithm output should be consistent (within a predetermined tolerance; coherent). Metric: $M=\{0,1\}$, where 0 is assigned for cases without discrepancies between the algorithm output and the report, and 1 is assigned for cases with discrepancies between the algorithm output and the report. A discrepancy can occur: (a) between a given case and a report obtained at the same time; (b) between a prior exam and a current report; or (c) between a current exam and a prior report.

Some embodiments of the present invention operate in fields of endeavor other than in the medical field. Some embodiments apply the methods of supplying training images described herein, to machine deep learning training methods in the fields of materials science, quality control, failure analysis, astronomy, signal processing or analysis, to name but a few examples.

In the field of failure analysis, for example, in some embodiments, an automated image analysis tool analyzes a series of optical and electron micrographs to classify the nature of a failure in a case of a failed integrated circuit chip. If a conclusion cannot be reached with a sufficient degree of confidence, the analysis tool classifies the case as "interesting" and passes the case to a reviewing workstation where a team of material scientists, engineers and/or other specialists arrive at a conclusion as to a contributing cause of the failure. Once dispositioned, the reviewing workstation passes the resulting data and conclusion to the automated image analysis tool where the tool incorporates the data into a knowledge base to improve analyses of similar cases in the future, and reduce the frequency of "interesting" cases needing human intervention for proper disposition.

Some embodiments of the present invention comprise a system that: (i) receives data for computing clinically relevant features on medical images; (ii) computes a degree of interest in a case to be collected for further analysis and/or engineering purposes; (iii) identifies and maintains a list of the most interesting cases (cases with a relatively high (above a threshold) degree of interest); (iv) provides a means to send those data directly to a third party (such as research and development teams, annotators, medical specialists, etc.) for collection and/or further analysis; and/or (v) provides a means to receive analyzed results from the third party.

The system computes a degree of interest based on intermediate metrics of an image processing algorithm and/or by comparing clinically relevant features (for example, evidence of a given disease) with a second source of information (for example, classification by a medical specialist) to search for discrepancies (for example, where the image processing algorithm determines there is evidence of a given disease, but the second source determines there is not evidence of the disease). In some embodiments, the second source of information is derived from radiologist interaction with a case, for example by analyzing an image that is displayed on a viewer. The system provides for an end user (the radiologist or other specialist) to give feedback on the case (for example, by clicking on a button to indicate that there is nothing relevant in the case, or by highlighting an area in an image needing further analysis and consideration).

The system automatically analyzes end user interactions with the viewer (for example, list of successive actions, review time, case dispositions, etc.) to estimate or classify outcome of a case (for example, spending an unusually long amount of time (for example, longer than a mean plus three standard deviations) on a case may decrease confidence in the outcome, whereas spending an average (or less) amount of time may increase confidence). The system further analyzes end user action to pre-localize findings of interests (for example, to focus attention on a specific area for further analysis).

In some embodiments, an image processing algorithm attempts to detect and/or classify findings in an image or the image itself.

In some embodiments, an image processing algorithm comprises at least a classifier (or classifier algorithm), and an intermediate metric is a lack of confidence (for example, a confidence statistic that is below a threshold) with respect to the classifier output.

In some embodiments, an image processing algorithm comprises at least a detection algorithm, and an intermediate metric is a lack of confidence (for example, a confidence statistic that is below a threshold) of the detection algorithm output.

In some embodiments, the image processing algorithm uses at least one lower dimensioned representation (for example, a three-dimensional model projected (partially or fully) onto at least one two-dimensional plane) of the input image, and an intermediate metric is derived from a probability that the input image is an outlier (probability of occurrence being below a threshold) compared to the distribution of data used for the design of the image processing algorithm (for example, training of a deep learning network or regression of a more simplistic model).

In some embodiments, at least one stage of the image processing algorithm comprises an ensemble (a group of deep learning algorithms working in concert with one another) of deep learning models and/or algorithms, and an intermediate metric is based on a discrepancy of outputs among and between the algorithms of the ensemble.

In some embodiments, the second source of information is a report from the user indicating saying what is to be found in the input images. Input images may be one, or any combination of: patient pathology(ies), finding localization(s), and/or finding characterization(s)

In some embodiments of the present invention, a first source of information comprises a relevant feature extracted from image by an image processing algorithm. A second source of information comprises output from a review algorithm (in conjunction with a user interaction), where derived metrics produced therefrom are discordant (inconsistent) with the original extracted relevant features determined by the image processing algorithm.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

IV. DEFINITIONS

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

Including/include/includes: unless otherwise explicitly noted, means "including but not necessarily limited to."

User/subscriber: includes, but is not necessarily limited to, the following: (i) a single individual human; (ii) an artificial intelligence entity with sufficient intelligence to act as a user or subscriber; and/or (iii) a group of related users or subscribers.

Data communication: any sort of data communication scheme now known or to be developed in the future, including wireless communication, wired communication and communication routes that have wireless and wired portions; data communication is not necessarily limited to: (i) direct data communication; (ii) indirect data communication; and/or (iii) data communication where the format, packetization status, medium, encryption status and/or protocol remains constant over the entire course of the data communication.

Receive/provide/send/input/output/report: unless otherwise explicitly specified, these words should not be taken to imply: (i) any particular degree of directness with respect to the relationship between their objects and subjects; and/or (ii) absence of intermediate components, actions and/or things interposed between their objects and subjects.

Without substantial human intervention: a process that occurs automatically (often by operation of machine logic, such as software) with little or no human input; some examples that involve "no substantial human intervention" include: (i) computer is performing complex processing and a human switches the computer to an alternative power supply due to an outage of grid power so that processing continues uninterrupted; (ii) computer is about to perform resource intensive processing, and human confirms that the resource-intensive processing should indeed be undertaken (in this case, the process of confirmation, considered in isolation, is with substantial human intervention, but the resource intensive processing does not include any substantial human intervention, notwithstanding the simple yes-no style confirmation required to be made by a human); and (iii) using machine logic, a computer has made a weighty decision (for example, a decision to ground all airplanes in anticipation of bad weather), but, before implementing the weighty decision the computer must obtain simple yes-no style confirmation from a human source.

Automatically: without any human intervention.

Module/Sub-Module: any set of hardware, firmware and/or software that operatively works to do some kind of function, without regard as to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, and/or application-specific integrated circuit (ASIC) based devices.

What is claimed is:

1. A computer-implemented method comprising:
analyzing a first set of images, including a first image, at an image manipulation stage of an image processing algorithm, wherein the image manipulation stage comprises an image processing algorithmic chain;
extracting a plurality of relevant features derived from the analysis at the image manipulation stage, including a first extracted relevant feature with respect to the first image;
computing a plurality of degrees of interest, including a first degree of interest, with respect to the plurality of extracted relevant features, wherein a respective degree of interest inversely correlates to a degree of confidence associated with the analysis;
determining a subset of the plurality of extracted relevant features from the first set of images wherein a respectively corresponding plurality of degrees of interest exceed a threshold; and
in response to determining the subset of the plurality of extracted relevant features from the first set of images, sending the subset of the first set of images to a receiving system.

2. The method of claim 1, wherein:
the image processing algorithmic chain comprises at least one internal operation selected from the group consisting of: detecting a finding in the first image, classifying the finding in the first image, and classifying the first image; and
the plurality of degrees of interest are based on a plurality of features derived from an output of the internal operation, wherein the output is selected from the group consisting of: a final output, and an intermediate output.

3. The method of claim 2 wherein:
the plurality of features are associated with respectively corresponding measures of confidence with respect to an output of the at least one internal operation;
the at least one internal operation implements a model selected from the group consisting of a deep learning model, and a regression model; and
the measures of confidence are based on a plurality of values selected from the group consisting of:
a distance between the output of the detecting a finding operation, and a given value,
a distance between the output of the classifying a finding operation, and a given value,
a discrepancy among a plurality of outputs of a respectively corresponding plurality of operations that perform a same task, and
a probability of the input data, of an internal operation, to be represented in data used for training the deep learning model corresponding to the internal operation.

4. The method of claim 1, wherein computing the first degree of interest further comprises:
comparing information with respect to the first extracted relevant feature against a second source of information based on a user input; and
determining a discrepancy exists between the information with respect to the first extracted relevant feature and the second source of information;
wherein:
the second source of information comprises information with respect to a plurality of images selected from the group consisting of patient pathologies, finding localizations, and finding characterizations.

5. The method of claim 1, wherein
the image manipulation stage comprises displaying for review the first image, on a system comprising a user interface for user interaction with a displayed image; and
the first degree of interest is based on an analysis of a user interaction with respect to the first image.

6. The method of claim 5, further comprising:
generating an analysis result based on an aspect of the user interaction;
wherein the aspect of the user interaction is selected from the group consisting of:
a time interval duration over which the user interaction takes place, a first user input causing the display device to magnify the image,
a second user input causing the display device to shrink the image,
a third user input causing the display device to focus on a selected area of the image,
a fourth user input causing a second measurement to be taken with respect to an aspect of the first image, and
a fifth user input comprising an annotation and associating the annotation with the image.

7. The method of claim 6, further comprising:
pre-localizing a finding of interest with respect to the first image based on the aspect of the user interaction.

8. A computer program product comprising:
one or more computer readable storage media, and program instructions collectively stored on the one or more computer readable storage media, the program instructions comprising program instructions programmed to perform:
analyzing a first set of images, including a first image, at an image manipulation stage of an image processing algorithm, wherein the image manipulation stage comprises an image processing algorithmic chain;
extracting a plurality of relevant features derived from the analysis at the image manipulation stage, including a first extracted relevant feature with respect to the first image;
computing a plurality of degrees of interest, including a first degree of interest, with respect to the plurality of extracted relevant features, wherein a respective degree of interest inversely correlates to a degree of confidence associated with the analysis;
determining a subset of the plurality of extracted relevant features from the first set of images wherein a respectively corresponding plurality of degrees of interest exceed a threshold; and
in response to determining the subset of the plurality of extracted relevant features from the first set of images, sending the subset of the first set of images to a receiving system.

9. The computer program product of claim 8, wherein:
the image processing algorithmic chain comprises at least one internal operation selected from the group consisting of: detecting a finding in the first image, classifying the finding in the first image, and classifying the first image; and
the plurality of degrees of interest are based on a plurality of features derived from an output of the internal operation, wherein the output is selected from the group consisting of: a final output, and an intermediate output.

10. The computer program product of claim 9 wherein:
the plurality of features are associated with respectively corresponding measures of confidence with respect to an output of the at least one internal operation;
the at least one internal operation implements a model selected from the group consisting of a deep learning model, and a regression model; and
the measures of confidence are based on a plurality of values selected from the group consisting of:
a distance between the output of the detecting a finding operation and a given value,
a distance between the output of the classifying a finding operation and a given value,
discrepancies between a plurality of outputs of a respectively corresponding plurality of operations that perform a same task, and
a probability of the input data, of an internal operation, to be represented in data used for training the deep learning model corresponding to the internal operation.

11. The computer program product of claim 8, wherein computing the first degree of interest further comprises program instructions programmed to perform:
comparing information with respect to the first extracted relevant feature against a second source of information based on a user input; and
determining a discrepancy exists between the information with respect to the first extracted relevant feature and the second source of information;
wherein:
the second source of information comprises information with respect to a plurality of images selected from the group consisting of patient pathologies, finding localizations, and finding characterizations.

12. The computer program product of claim 8, wherein:
the image manipulation stage comprises displaying for review the first image, on a system comprising a user interface for user interaction with a displayed image; and
the first degree of interest is based on an analysis of a user interaction with respect to the first image.

13. The computer program product of claim 12, further comprising program instructions programmed to perform:
generating an analysis result based on an aspect of the user interaction;
wherein the aspect of the user interaction is selected from the group consisting of:
a time interval duration over which the user interaction takes place,
a first user input causing the display device to magnify the image,
a second user input causing the display device to shrink the image,
a third user input causing the display device to focus on a selected area of the image,
a fourth user input causing a second measurement to be taken with respect to an aspect of the first image, and
a fifth user input comprising an annotation and associating the annotation with the image.

14. The computer program product of claim 13, further comprising program instructions programmed to perform:
pre-localizing a finding of interest with respect to the first image based on the aspect of the user interaction.

15. A computer system comprising:
a processor set; and
one or more computer readable storage media;
wherein:
the processor set is structured, located, connected and/or programmed to run program instructions stored on the one or more computer readable storage media; and
the program instructions include program instructions programmed to perform:
analyzing a first set of images, including a first image, at an image manipulation stage of an image processing algorithm, wherein the image manipulation stage comprises an image processing algorithmic chain;
extracting a plurality of relevant features derived from the analysis at the image manipulation stage, including a first extracted relevant feature with respect to the first image;

computing a plurality of degrees of interest, including a first degree of interest, with respect to the plurality of extracted relevant features, wherein a respective degree of interest inversely correlates to a degree of confidence associated with the analysis;

determining a subset of the plurality of extracted relevant features from the first set of images wherein a respectively corresponding plurality of degrees of interest exceed a threshold; and in response to determining the subset of the plurality of extracted relevant features from the first set of images, sending the subset of the first set of images to a receiving system.

16. The computer system of claim 15, wherein:

the image processing algorithmic chain comprises at least one internal operation selected from the group consisting of: detecting a finding in the first image, classifying the finding in the first image, and classifying the first image; and the plurality of degrees of interest are based on a plurality of features derived from an output of the internal operation, wherein the output is selected from the group consisting of: a final output, and an intermediate output.

17. The computer system of claim 16 wherein:

the plurality of features are associated with respectively corresponding measures of confidence with respect to an output of the at least one internal operation;

the at least one internal operation implements a model selected from the group consisting of a deep learning model, and a regression model; and the measures of confidence are based on a plurality of values selected from the group consisting of:
- a distance between the output of the detecting a finding operation and a given value,
- a distance between the output of the classifying a finding operation and a given value,
- discrepancies between a plurality of outputs of a respectively corresponding plurality of operations that perform a same task, and
- a probability of the input data, of an internal operation, to be represented in data used for training the deep learning model corresponding to the internal operation.

18. The computer system of claim 15, wherein computing the first degree of interest further comprises program instructions programmed to perform:

comparing information with respect to the first extracted relevant feature against a second source of information based on a user input; and determining a discrepancy exists between the information with respect to the first extracted relevant feature and the second source of information;

wherein:
the second source of information comprises information with respect to a plurality of images selected from the group consisting of patient pathologies, finding localizations, and finding characterizations.

19. The computer system of claim 15, wherein:

the image manipulation stage comprises displaying for review the first image, on a system comprising a user interface for user interaction with a displayed image; and the first degree of interest is based on an analysis of a user interaction with respect to the first image.

20. The computer system of claim 19, further comprising program instructions programmed to perform:

generating an analysis result based on an aspect of the user interaction; and pre-localizing a finding of interest with respect to the first image based on the aspect of the user interaction;

wherein the aspect of the user interaction is selected from the group consisting of:
- a time interval duration over which the user interaction takes place,
- a first user input causing the display device to magnify the image,
- a second user input causing the display device to shrink the image,
- a third user input causing the display device to focus on a selected area of the image,
- a fourth user input causing a second measurement to be taken with respect to an aspect of the first image, and
- a fifth user input comprising an annotation and associating the annotation with the image.

* * * * *